(12) United States Patent
Lange

(10) Patent No.: US 6,372,517 B1
(45) Date of Patent: Apr. 16, 2002

(54) MAGNETIC PARTICLES WITH BIOLOGICALLY ACTIVE RECEPTORS

(75) Inventor: Hans Lange, Lamberheim (DE)

(73) Assignee: Innova-Gesellschaft zur Entwicklung und Vermarktung innovativer Produkte m.b.H., Mannheim (DE)

( * ) Notice: Subject to any disclaimer, the term of this patent is extended or adjusted under 35 U.S.C. 154(b) by 0 days.

(21) Appl. No.: 09/445,984

(22) PCT Filed: Jun. 18, 1997

(86) PCT No.: PCT/DE97/01300

§ 371 Date: Dec. 17, 1999

§ 102(e) Date: Dec. 17, 1999

(87) PCT Pub. No.: WO98/58257

PCT Pub. Date: Dec. 23, 1998

(51) Int. Cl.⁷ ..................... G01N 33/553; G01N 33/53; C04B 1/32

(52) U.S. Cl. ................ 436/526; 436/518; 436/519; 436/523; 436/524; 436/525; 436/528; 436/532; 436/535; 436/536; 436/538; 436/8; 436/65; 436/73; 436/824; 435/7.5; 435/7.1; 435/7.2; 435/28; 435/4; 106/415; 106/417; 106/441; 106/459

(58) Field of Search .................. 436/526, 518, 436/519, 523–525, 528, 532, 536, 535, 8, 65, 73, 538, 824; 435/7.5, 28, 4, 7.1, 7.2; 106/415, 417, 441, 459

(56) References Cited

U.S. PATENT DOCUMENTS

| | | | | |
|---|---|---|---|---|
| 3,861,946 A | * | 1/1975 | Waikins et al. ............. | 117/100 |
| 3,926,659 A | * | 12/1975 | Bernhard et al. ............ | 106/291 |
| 3,970,518 A | | 7/1976 | Giaever ..................... | 195/1.5 |
| 4,038,099 A | * | 7/1977 | DeLuca, Jr. et al. ........ | 106/291 |
| 4,055,377 A | * | 10/1977 | Erickson et al. ............ | 350/105 |
| 4,146,403 A | * | 3/1979 | Armanini et al. ........... | 106/291 |
| 4,192,691 A | * | 3/1980 | Armanini .................... | 106/291 |
| 4,344,987 A | * | 8/1982 | Ostertag et al. ............ | 427/213 |
| 4,725,499 A | * | 2/1988 | Itoh et al. ................... | 428/361 |
| 4,795,698 A | | 1/1989 | Owen et al. .................. | 435/4 |
| 4,867,793 A | * | 9/1989 | Franz et al. ................ | 106/415 |
| 4,867,795 A | * | 9/1989 | Ostertag et al. ............ | 106/459 |
| 4,868,106 A | * | 9/1989 | Ito et al. ........................ | 435/7 |
| 4,883,539 A | * | 11/1989 | Mattila et al. .............. | 106/417 |
| 4,976,787 A | * | 12/1990 | Ito et al. ..................... | 106/441 |
| 5,061,317 A | * | 10/1991 | Korpi et al. ................. | 106/417 |
| 5,223,360 A | * | 6/1993 | Prengel et al. ................ | 430/39 |
| 5,320,944 A | * | 6/1994 | Okada et al. ................... | 435/7 |
| 5,508,164 A | * | 4/1996 | Kausch et al. ................. | 435/6 |
| 5,576,185 A | * | 11/1996 | Coulter et al. ............. | 435/7.23 |
| 5,643,721 A | * | 7/1997 | Spring et al. .................. | 435/6 |
| 5,698,839 A | * | 12/1997 | Jagielinski et al. ......... | 235/493 |
| 5,705,265 A | * | 1/1998 | Clough et al. .............. | 428/307 |
| 5,763,085 A | * | 6/1998 | Atarashi et al. ............ | 428/403 |
| 5,855,790 A | * | 1/1999 | Bradbury et al. ........... | 210/676 |
| 5,935,866 A | * | 8/1999 | Chagnon et al. ............ | 436/526 |
| 6,001,526 A | * | 12/1999 | Nishikawa et al. ...... | 430/106.6 |
| 6,045,914 A | * | 4/2000 | Sullivan et al. ............. | 428/404 |
| 6,048,574 A | * | 4/2000 | Atarashi et al. ............ | 427/127 |
| 6,103,537 A | * | 8/2000 | Ullman et al. .............. | 436/526 |
| 6,165,260 A | * | 12/2000 | Gale .......................... | 106/439 |

FOREIGN PATENT DOCUMENTS

DE 196 06 598 11/1997 ......... G01N/33/551

\* cited by examiner

*Primary Examiner*—Long V. Le
*Assistant Examiner*—Pensee T. Do
(74) *Attorney, Agent, or Firm*—Fish & Richardson P.C., P.A.

(57) ABSTRACT

Magnetic particles for separating biological mixtures consist of nacreous luster pigments with magnetic properties coated with a biological polymer.

16 Claims, No Drawings

MAGNETIC PARTICLES WITH BIOLOGICALLY ACTIVE RECEPTORS

The invention relates to magnetic particles for separating biological mixtures, to a process for preparing them and to a use of the magnetic particles.

From U.S. Pat. No. 3,970,518 it is known to use magnetic particles having different magnetic properties as a solid phase for separating biological mixtures. The particles are coated with a biological material. They are suitable, for example, for separating off defined cell populations from a mixture of different cell populations.

U.S. Pat. No. 4,795,698 discloses a process for preparing suspendable magnetic particles coated with a biological material. In that process, a coprecipitation is carried out from a solution comprising Fe(III) ions and a polymer, e.g., a protein, by addition in the case [sic] of a strong base, such as $NH_4OH$. The coprecipitate is resuspended, washed and then processed further to give a magnetic polymer material. The process has the disadvantage that iron ions are released.

The object of the present invention is to eliminate the disadvantages of the prior art. In particular, the intention is to provide magnetic particles, which are easy and inexpensive to prepare, for separating biological mixtures.

In accordance with the invention, magnetic particles, for separating biological mixtures, are provided which comprise pearl luster color pigments having magnetic properties and a biological polymer coating. Pearl luster color pigments are inexpensive base starting materials which are produced on the industrial scale in particle form for the coatings industry. They comprise mica leaflets, possibly with a coating of various metal oxides, such as hematite or titanium oxide.

In the case of magnetic pearl luster color pigments, a mica core is enveloped first with titanium oxide and then with magnetite. This so-called black pigment possesses ferromagnetic properties. It is available in particle size distributions of typically 10–60 μm, preferably in particle sizes of 1–30 μm. The black pigment typically has the following composition:

mica 38–48% by weight
titanium dioxide 5–9% by weight
magnetite 47–53% by weight The black pigment can, surprisingly, be coated directly with biological polymers. In this form it is suitable for separating biological mixtures.

A further surprising property of the magnetic pearl luster color pigments is their resistance to acids, such as glacial acetic acid, alkalis, such as sodium hydroxide, and to organic and inorganic solvents, such as dimethyl sulfoxide/water mixtures, acetone, alcohols, cellulose thinners, methylene chloride and the like. The magnetic behavior of the particles of the invention is unaffected by the aforementioned substances.

The particles of the invention are preferably employed in combinatorial chemistry and in high throughput screening. They can be used in particular as solid phase supports for organic reactions.

In the case of reactions requiring extreme solvents, the biological polymer coating is not resistant. It has surprisingly been found that black pigments can be used as solid phase supports in combinatorial chemistry or in high throughput screening. They can be used, further, as catalysts.

The invention is elucidated further below with reference to an exemplary embodiment.

1. Preparation of Biotinylated Bovine Immunoglobulin G (b-IgG)

To prepare biotinylated bovine immunoglobulin, 0.5 ml of a b-IgG solution containing 2 mg of b-IgG (Boehringer Mannheim) dissolved in 1 ml of phosphate-buffered saline solution, pH 7.25 (2.76 g/l $NaH_2PO_4*H_2O$; 3.56 g/l $Na_2HPO_4*2H_2O$; 8 g/l NaCl) are mixed with a 6 μl D-biotinoyl-ε-aminocaproic N-hydroxysuccinimide ester solution in phosphate-buffered saline solution, pH 7.25, and DMSO (Biotin Labeling Kit from Beohringer [sic] Mannheim. The mixture is stirred at room temperature for 2.5 h by means of a magnetic stirrer and is then left to stand overnight. The molar ratio of biotin b-IgG corresponds to 20:1.

2. Coating of Magnetic Particles with Biotinylated b-IgG 2 g of "4898 Iriodin® Black Mica" (Merck Catalog No. 4898.00050) are suspended in a solution of 40 ml of coating buffer ($NaHCO_3$, 4.2 g/l, pH 9.6) and 6 μl of b-IgG-biotin solution as in section 1 and the suspension is incubated overnight using a mechanical stirrer such that the suspension remains intact as a result of gentle movement.

The particles are subsequently washed 3× with 100 ml of Milli-Q water each time, the separation of solid and liquid phase taking place by a sedimentation or centrifugation between each of the washing steps. The particles are subsequently taken up again in 40 ml of phosphate-buffered saline solution, pH 7.25.

3. Coating of Magnetic Particles with b-IgG

For the control, a batch with nonbiotinylated b-IgG is carried out under identical concentration conditions as in the case of Section 2.

4. Testing of the Binding Capacity

To test the binding capacity, 200 μl of the fully suspended magnetic particles as per section 2 are mixed with 200 μl of a streptavidin peroxidase conjugate solution (Boehringer Mannheim Catalog No.: 1089 153) diluted 1:20,000 in phosphate-buffered saline solution, pH 7.25, and the mixture is incubated for 45 minutes with shaking. The particles are subsequently separated off by means of a magnetic separator (Boehringer Mannheim Order No. 1 641 794) and the supernatant is discarded. This procedure is repeated. Then 220 μl of ABTS® solution (Boehringer Mannheim Catalog No. 1 204 530 and 1 112 422) are added and incubation is carried out for 15 minutes following resuspension. The particles are separated off using a magnetic separator. 200 μl of the supernatant are transferred to a microtiter plate (Innova GmbH) and measured by transmission photometry at 405 nm

| Result | |
|---|---|
| Magnetic particles with b-IgG biotin (as per section 2) | 850 mE |
| Control with b-IgG (as per section 3) | 210 mE |

What is claimed is:

1. Magnetic particles for separating biological mixtures, wherein the magnetic particles comprise pearl luster color pigments and a biological polymer coating, wherein the pearl luster color pigments have magnetic properties.

2. Magnetic particles according to claim 1, wherein the polymer coating is a protein.

3. Magnetic particles according to claim 2, wherein the protein is a binding protein.

4. Magnetic particles according to claim 3, wherein the binding protein is an antibody.

5. Magnetic particles according to claim 3, wherein the binding protein comprises streptavidin.

6. Magnetic particles according to claim 2, wherein the protein comprises a receptor.

7. Magnetic particles according to claim 2, wherein the protein is an antigen.

8. Magnetic particles according to claim 1, wherein the pearl luster color pigments comprise a mica core, wherein the mica core is surrounded by at least one metal oxide, wherein the at least one metal oxide has magnetic properties.

9. Magnetic particles according to claim 1, wherein the particles have a size distribution of 0.1–500 µm.

10. Magnetic particles according to claim 9, wherein the pearl luster color pigments are present in a particle size distribution of 1–60 µm.

11. A method of separating one or more components in a biological mixture from the remainder of the biological mixture, comprising the steps of:

(a) contacting the magnetic particles of claim 1 with a biological mixture, wherein the biological mixture comprises one or more components, wherein the component(s) have an affinity for the biological polymer coating, to thereby form component-associated particles;

(b) applying a magnetic force to the component-associated particles; and (c) separating the component-associated particles from the remainder of the biological mixture.

12. The method of claim 11, further comprising the steps of:

(d) washing the separated component-associated particles of step (c) with a wash solution;

(e) applying a magnetic force to the washed component-associated particles of step (d).

13. The method of claim 12, wherein the wash solution is selected from the group consisting of a strongly acidic medium, a strongly basic medium and an organic solvent.

14. The method of claim 11, wherein the biological polymer coating is biotinylated bovine IgG.

15. The method of claim 14, wherein the component is a protein.

16. A method of preparing magnetic particles for separating biological mixtures, wherein the particles comprise pearl luster color pigments, wherein the pearl luster color pigments have magnetic properties, comprising the step of coating the particles with a biological material.

* * * * *